US008242084B2

(12) United States Patent
Sugiyama et al.

(10) Patent No.: US 8,242,084 B2
(45) Date of Patent: Aug. 14, 2012

(54) DIMERIZED PEPTIDE

(75) Inventors: Haruo Sugiyama, Minoo (JP); Hideo Takasu, Nishinomiya (JP); Fumio Samizo, Suita (JP)

(73) Assignees: Chugai Seiyaku Kabushiki Kaisha, Tokyo-to (JP); Dainippon Sumitomo Pharma Co., Ltd., Osaka-shi (JP); International Institute of Cancer Immunology, Inc., Suita-shi (JP)

( * ) Notice: Subject to any disclaimer, the term of this patent is extended or adjusted under 35 U.S.C. 154(b) by 0 days.

(21) Appl. No.: 12/795,187

(22) Filed: Jun. 7, 2010

(65) Prior Publication Data
US 2010/0292164 A1 Nov. 18, 2010

Related U.S. Application Data

(63) Continuation of application No. 10/541,821, filed as application No. PCT/JP2004/000254 on Jan. 15, 2004, now abandoned.

(30) Foreign Application Priority Data

Jan. 15, 2003 (JP) ................................ 2003-007122

(51) Int. Cl.
A61K 38/00 (2006.01)
(52) U.S. Cl. ..................................... 514/21.4
(58) Field of Classification Search .................. None
See application file for complete search history.

(56) References Cited

U.S. PATENT DOCUMENTS

| 6,034,235 | A | 3/2000 | Sugiyama et al. | |
| 6,277,832 | B1 | 8/2001 | Sugiyama et al. | |
| 7,030,212 | B1 * | 4/2006 | Sugiyama et al. | 530/328 |
| 7,063,854 | B1 | 6/2006 | Gaiger et al. | |
| 7,326,767 | B1 * | 2/2008 | Stauss et al. | 530/300 |
| 2004/0097703 | A1 | 5/2004 | Sugiyama | |
| 2004/0247609 | A1 | 12/2004 | Sugiyama | |
| 2005/0002951 | A1 | 1/2005 | Sugiyama et al. | |
| 2005/0266014 | A1 | 12/2005 | Sugiyama et al. | |
| 2008/0070835 | A1 | 3/2008 | Sugiyama | |
| 2008/0152631 | A1 | 6/2008 | Sugiyama | |
| 2009/0099090 | A1 | 4/2009 | Sugiyama et al. | |

FOREIGN PATENT DOCUMENTS

| EP | 1 103 564 | 5/2001 |
| EP | 1371664 | 12/2003 |
| WO | 00/18795 | 4/2000 |
| WO | WO-00/18795 | 4/2000 |
| WO | 02/079253 | 10/2002 |
| WO | WO-02/79253 | 10/2002 |

OTHER PUBLICATIONS

Di Modugno et al., J. Immunother., 1997, vol. 20, No. 6, pp. 431-436.
Marastoni, M. et al., Eur. J. Med. Chem., 2000, vol. 35, No. 6, pp. 593-598.
Demer (Bio/Tchnology, 1994, 12:320).
Gura (Science, 1997, 278:1041-1042).
Di Modugno et al. "MHC-Peptide Binding: Dimers of Cysteine-Containing Nonapeptides Bind with High Affinity to HLA-A2.1 Class I Molecules", Journal of Immunotherapy, vol. 20, No. 6, pp. 431-436 1997.
Marastoni et al. "Design of dimeric peptides obtained from a subdominant Epstein-Barr virus LMP2-derived epitope", Eur. J. Med. Chem., vol. 35, pp. 593-598 2000.
Oka et al. "Cancer Immunotherapy Targeting Wilms' Tumor Gene WT1 Product", Journal of Immunology, vol. 164, pp. 1873-1880 2000.
Tsuboi et al. "Cytotoxic T-Lymphocyte Responses Elicited to Wilms' Tumor Gene WT1 Product by DNA Vaccination", Journal of Clinical Immunology, vol. 20, No. 3, pp. 195-202 2000.
Rosenberg. "A New Era for Cancer Immunotherapy Based on the Genes that Encode Cancer Antigens", Immunity, vol. 10, pp. 281-287 1999.
Bakker et al. "Melanocyte Lineage-specific Antigen gp100 is Recognized by Melanoma-derived Tumor-infiltrating Lymphocytes", Journal of Experimental Medicine, vol. 179, pp. 1005-1009 1994.
Kawakami et al. "Cloning of the gene coding for a shared human melanoma antigen recognized by autologous T cells infiltrating into tumor", Proc. Natl. Acad. Sci., vol. 91, pp. 3515-3519 1994.
Brichard et al. "The Tyrosinase Gene Codes for an Antigen Recognized by Autologous Cytolytic T Lymphocytes on HLA-A2 Melanomas", J. Exp. Med., vol. 178, pp. 489-495 1993.
Fisk et al. "Identification of an Immunodominant Peptide of HER-2/neu Protooncogene Recognized by Ovarian Tumor-specific Cytotoxic T Lymphocyte Lines", J. Exp. Med., vol. 181, pp. 2109-2117 1995.
Tsang et al. "Generation of Human Cytotoxic T Cells Specific for Human Carcinoembryonic Antigen Epitopes From Patients Immunized with Recombinant Vaccinia-CEA Vaccine", Journal of the National Cancer Institute, vol. 87, No. 13, pp. 982-990 1995.
Correale et al. "In Vitro Generation of Human Cytotoxic T Lymphocytes Specific for Peptides Derived from Prostate-Specific Antigen", Journal of the National Cancer Institute, vol. 89, No. 4, pp. 293-300 1997.
Melief et al. "Potential Immunogenicity of oncogene and tumor suppressor gene products", Current Opinion in Immunology, vol. 5, pp. 709-713 1993. Pardoll. "New strategies for enhancing the immunogenicity of tumors", Current Opinion in Immunology, vol. 5, pp. 719-725 1993.
Nanda et al. "Induction of Anti-Self-Immunity to Cure Cancer", Cell, vol. 82, pp. 13-17 1995.
Melief et al. "T-Cell Immunotherapy of Tumors by Adoptive Transfer of Cytotoxic T Lymphocytes and by Vaccination with Minimal Essential Epitopes", Immunological Reviews, No. 146, pp. 167-177 1995.
Call et al. "Isolation and Characterization of a Zinc Finger Polypeptide Gene at the Human Chromosome 11 Wilms'Tumor Locus", Cell, vol. 60, pp. 509-520 1990.
Gessler et al. "Homozygous deletion in Wilms tumours of a zinc-finger gene identified by chromosome jumping", Nature, vol. 343, pp. 774-778 1990.
Jain (Sci. Am., 1994,271:58-65).
Essell (J. NIH Res. 1995-7:46).
Spitler (Cancer Biotherapy, 1995, 10:1-3).
Boon (Adv. Can. Res. 19921-58:177-210).
Freshney (Culture of Animal Cells, a manual of Basic Technique, Alan R. Liss, Inc., 1983, New York, p. 4.).

* cited by examiner

Primary Examiner — Sheela J Huff
(74) Attorney, Agent, or Firm — Oblon, Spivak, McClelland, Maier & Neustadt, L.L.P.

(57) ABSTRACT

The present invention provides a novel tumor antigen peptide and its cancer vaccine, specifically, a peptide dimer wherein two peptide monomers consisting of 7-30 amino acids including at least one cysteine residue and being capable of producing a tumor antigen peptide are bound each other through a disulfide bond.

4 Claims, 1 Drawing Sheet

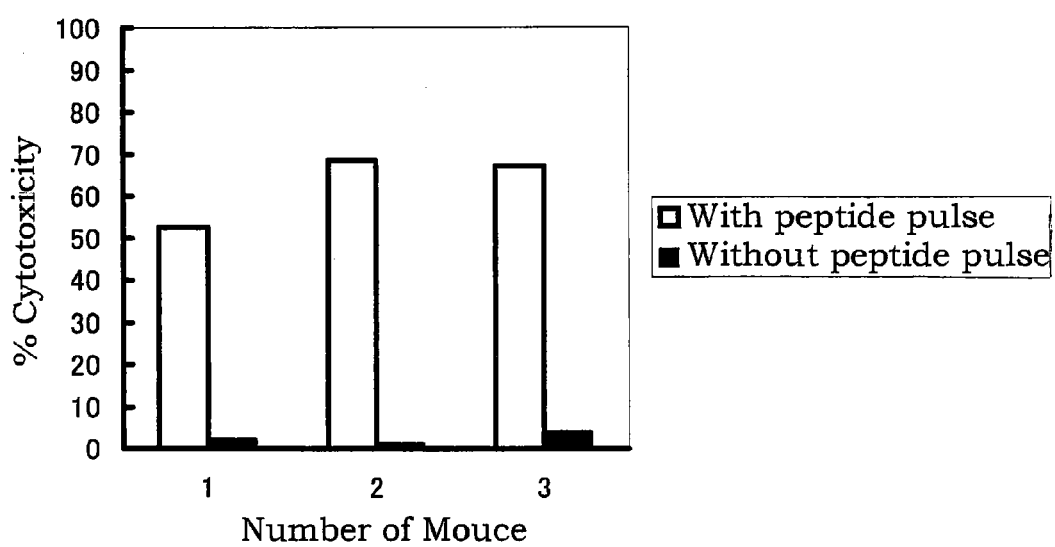

ID NO: 72)
DIMERIZED PEPTIDE

CROSS-REFERENCE TO RELATED APPLICATIONS

This application is a continuation application of U.S. Ser. No. 10/541,821 filed Jul. 11, 2005, abandoned, which was a National Stage of PCT/JP2004/000254 filed Jan. 15, 2004 and claims the benefit of JP 2003-007122 filed Jan. 15, 2003.

TECHNICAL FIELD

The present invention relates to cancer vaccine therapy, more particularly to a peptide dimer which can produce a tumor antigen peptide having activity of inducing cytotoxic T cells, and a pharmaceutical composition comprising the same.

BACKGROUND ART

The cell mediated immunity, particularly a cytotoxic T cell (hereinafter, referred to as "CTL") plays a significant role in the in vivo rejection of tumor cells or virus-infected cells. CTLs recognize a complex between an antigen peptide ("tumor antigen peptide") derived from a tumor antigen protein and an MHC (major histocompatibility complex) class I antigen, which is referred to as "HLA antigen" in the case of human, on a cancer cell, and attack and kill the cell.

Typical examples of tumor antigen proteins include those listed in the Table of Immunity, vol. 10:281, 1999. Specific examples include the melanosome antigens such as melanocyte tissue-specific protein gp 100 (J. Exp. Med., 179: 1005, 1994), MART-1 (Proc. Natl. Acad. Sci. USA, 91:3515, 1994) and tyrosinase (J. Exp. Med., 178: 489, 1993), and tumor markers as antigen proteins other than melanoma such as HER2/neu (J. Exp. Med., 181: 2109, 1995), CEA (J. Natl. Cancer. Inst., 87:982, 1995) and PSA (J. Natl. Cancer. Inst., 89:293, 1997).

A tumor antigen peptide is a peptide of around 8 to 11 amino acids that can be produced by intracellular processing of a tumor antigen protein by a protease in cells (Cur. Opin, Immunol., 5: 709, 1993; Cur. Opin, Immunol., 5: 719, 1993; Cell, 82: 13, 1995; Immunol. Rev., 146: 167, 1995). As described above, the so produced tumor antigen peptide is presented on the surface of a cell as a complex with an MHC class I antigen (HLA antigen) and recognized by CTLs. Accordingly, for the purpose of developing an immunotherapeutic agent for cancer (cancer vaccine) that makes use of the tumor cell destruction by CTLs, it is highly important to identify a tumor antigen peptide in a tumor antigen protein, which peptide is able to induce CTLs efficiently.

DISCLOSURE OF INVENTION

One of purposes of the present invention is to provide a novel tumor antigen derived from a tumor antigen peptide useful in vivo.

The present inventors have found that some peptides having been demonstrated to be a tumor antigen peptide contain a cysteine residue(s) and that a dimer composed of such peptides surprisingly show an activity of inducing CTLs ("CTL-inducing activity") equivalent to the monomer upon administration, and established the present invention.

Thus, the present invention encompasses the followings.
(1) A peptide dimer wherein two peptide monomers each consisting of 7-30 amino acids including at least one cysteine residue and being capable of producing a tumor antigen peptide having CTL-inducing activity are bound each other through a disulfide bond(s).
(2) The peptide dimer according to (1) above, which can produce a tumor antigen peptide having a CTL-inducing activity.
(3) The peptide dimer according to (1) or (2) above, wherein two peptide monomers are bound through one or two disulfide bonds.
(4) The peptide dimer according to any one of (1) to (3) above, wherein the peptide monomers are derived from WT 1 that is an expression product of tumor suppressor gene.
(5) The peptide dimer according to any one of (1) to (4) above, wherein the peptide monomer is as follows:

(SEQ ID NO: 72)
Cys Xaa Thr Trp Asn Gln Met Asn Xaa wherein Xaa at position 2 is an amino acid residue selected from Tyr, Phe, Met and Trp; and Xaa at position 9 is an amino acid residue selected from Phe, Leu, Ile, Trp and Met.
(6) The peptide dimer according to any one of (1) to (4) above, wherein the peptide monomer is selected from the following peptides.

(SEQ ID NO: 11)
Cys Met Thr Trp Asn Gln Met Asn Leu (SEQ ID NO: 18)
Asp Phe Lys Asp Cys Glu Arg Arg Phe (SEQ ID NO: 19)
Ala Tyr Pro Gly Cys Asn Lys Arg Tyr (SEQ ID NO: 20)
Asn Ala Pro Tyr Leu Pro Ser Cys Leu (SEQ ID NO: 21)
Gly Cys Asn Lys Arg Tyr Phe Lys Leu (SEQ ID NO: 22)
Arg Trp Pro Ser Cys Gln Lys Lys Phe (SEQ ID NO: 23)
Asp Ser Cys Thr Gly Ser Gln Ala Leu (SEQ ID NO: 44)
Cys Tyr Thr Trp Asn Gln Met Asn Leu (7) A pharmaceutical composition comprising a peptide dimer according to any one of (1) to (6) above together with a pharmaceutically acceptable carrier.
(8) The pharmaceutical composition according to (7) above which is used as a cancer vaccine.
(9) Use of a peptide dimmer according to any one of (1) to (6) above in the manufacture of a cancer vaccine.
(10) A method of treating or preventing cancer, which comprises administering a therapeutically effective amount of a peptide dimer according to any one of (1) to (6) above to a WT1-positive patient in need thereof.

BRIEF DESCRIPTION OF DRAWINGS

FIG. 1 is a graph showing that a peptide dimer (SEQ ID NO: 44) induces CTLs in transgenic mouse.

BEST MODE FOR CARRYING OUT THE INVENTION

In the peptide dimer of the present invention, two peptide monomers are dimerized through a disulfide bond(s) between SH groups of at least a pair of cysteine residues present in the peptide monomers.

The peptide dimer of the present invention has a CTL-inducing activity and the CTLs thus induced can exert an antitumor activity through the cytotoxic effects or the production of lymphokines. Accordingly, the peptide dimer of the present invention can be used as a cancer vaccine for treatment or prevention of cancers (tumors).

The peptide monomer constituting the peptide dimer of the present invention consists of 7-30 amino acid residues containing at least one cysteine residue, and produces a tumor antigen peptide having CTL-inducing activity. The phrase "produces a tumor antigen peptide" means that the peptide monomer has a characteristic of rendering a tumor antigen peptide capable of binding to an HLA antigen and being recognized by cytotoxic T cell (CTL). Any peptide monomer can be used in the present invention without limitation as far as it has a CTL-inducing activity; however, a peptide monomer which is derived from the tumor suppressor gene WT1 of human Wilms' tumor and comprises at least one cysteine residue is preferred. The tumor suppressor gene WT1 is expressed in various kinds of tumors (Cell, 60:509, 1990; NCBI data base Accession No. XP_034418, SEQ ID NO: 1). The WT1 gene was isolated from chromosome 11p13 as one of the causative genes of Wilms' tumors based on the analysis of the WAGR syndrome that was complicated by Wilms' tumors, aniridia, urogenital anomaly, mental retardation, etc. (Nature, 343: 774, 1990). The genomic DNA of WT1 is about 50 kb, and is composed of ten exons, and of which the cDNA is about 3 kb. The amino acid sequence deduced from the cDNA is as shown in SEQ ID NO: 1 (Cell., 60:509, 1990). The WT 1 gene has been suggested to promote the growth of leukemia cells from the facts that the WT1 gene is highly expressed in human leukemia, and that the leukemia cells are suppressed in their cellular growth by the treatment with WT1 antisense oligomers (JP-A-104627/1997). Then, the WT 1 gene has been demonstrated to be a new tumor antigen protein of leukemia and solid cancers (J. Immunol., 164: 1873-80, 2000, and J. Clin. Immunol., 20, 195-202, 2000) from the facts that the WT1 gene is also highly expressed in solid cancers such as gastric cancer, colon cancer, lung cancer, breast cancer, embryonal cancer, skin cancer, bladder cancer, prostate cancer, uterine cancer, cervical cancer, and ovarian cancer (JP-A-104627/1997, WO00/06602). Since cancer immunotherapy (cancer vaccine) is preferably applicable to as many cancer patients as possible, it is significant to identify tumor antigen peptides from WT 1 which is highly expressed in many kinds of cancers, and to develop cancer vaccines using the resultant tumor antigen peptides. In this regard, several natural-type tumor antigen peptides consisting of partial fragments of WT1 protein are described in WO00/06602 and WO00/18795; however, nothing has been known about their in vivo effects.

Other peptide monomers usable in the present invention include tumor antigen peptides containing at least one cysteine residue which are derived from tumor antigen proteins listed in the Table of Immunity, vol. 10:281, 1999.

The CTL-inducing activity can be confirmed by measuring the number of CTLs by HLA tetramer method (Int. J. Cancer: 100, 565-570 (2002)) or limiting dilution method (Nat. Med.: 4, 321-327 (1998)). Alternatively, for example, in the case of HLA-A24-restricted CTL-induction, the activity can be determined using HLA-A24 model mouse according to the method described in WO02/47474 or Int. J. Cancer: 100, 565-570 (2002).

The peptide monomer consists of 7-30, preferably 8-12, more preferably 9-11 amino acid residues. The peptide monomer preferably contains 1 or 2 cysteine resides taking into account both the motif for binding with HLA and the length of peptide.

The peptide monomer can be synthesized according to a method generally used in the field of peptide chemistry. Such a method can be found in literatures including Peptide Synthesis, Interscience, New York, 1966; The Proteins, Vol. 2, Academic Press Inc., New York, 1976; Peptide Synthesis, Maruzen, Inc., 1975; Peptide-Gosei no Kiso to Jikken, Maruzen, Inc., 1985; and Iyakuhin no Kaihatsu (Zoku), Vol. 14, Peptide Synthesis, Hirokawa-syoten, 1991.

The resultant peptide monomers can be allowed to form an intermolecular disulfide bond according to a method generally used in the peptide chemistry. The method for forming a disulfide bond can be found in literatures including Peptide Synthesis, Interscience, New York, 1966; The Proteins, Vol. 2, Academic Press Inc., New York, 1976; Peptide Synthesis, Maruzen, Inc., 1975; Peptide-Gosei no Kiso to Jikken, Maruzen, Inc., 1985; and Iyakuhin no Kaihatsu (Zoku), Vol. 14, Peptide Synthesis, Hirokawa-syoten, 1991.

Specifically, a peptide monomer containing one cysteine residue can be synthesized by, for example, removing all the protecting groups including the one on the cysteine side chain, and then subjecting the resulting monomer solution to air-oxidation under alkali condition, or forming a disulfide bond(s) by adding an oxidizing agent under alkali or acidic condition. Examples of oxidizing agent include iodine, dimethylsulfoxide (DMSO), potassium ferricyanide, and the like.

A monomer peptide containing two or more cysteine residues can be also synthesized according to the method described above. In this case, isomers resulting from disulfide bonds of different binding manner can be obtained. A peptide dimer wherein a disulfide bond is formed between intended cysteine residues can be prepared by selecting a particular combination of protecting groups for cysteine side chains. Examples of the combination of protecting groups include MeBzl (methylbenzyl) and Acm (acetamidomethyl) groups, Trt (trityl) and Acm groups, Npys (3-nitro-2-pyridylthio) and Acm groups, S-Bu-t (S-tert-butyl) and Acm groups, and the like. For example, in the case of a combination of MeBzl and Acm groups, the preparation can be carried out by a method comprising removing protecting groups other than MeBzl group and a protecting group(s) on the cysteine side chain, and subjecting the resulting monomer solution to air-oxidation to form a disulfide bond(s) between the deprotected cysteine residues, followed by deprotection and oxidization with iodine to form a disulfide bond(s) between the cysteine residues previously protected by Acm.

The resultant peptide dimer can be purified according to processes generally used in the field of peptide chemistry. Such a purification method can be found in literatures including Peptide Synthesis, Interscience, New York, 1966; The Proteins, Vol. 2, Academic Press Inc., New York, 1976; Peptide Synthesis, Maruzen, Inc., 1975; Peptide-Gosei no Kiso to Jikken, Maruzen, Inc., 1985; and Iyakuhin no Kaihatsu (Zoku), Vol. 14, Peptide Synthesis, Hirokawa-syoten, 1991. A method using HPLC is preferred.

The resultant peptide dimer of the present invention shows excellent stability against an oxidizing agent or the like in solution and possesses a given quality and CTL-inducing activity due to the disulfide bond(s) between cysteine residues.

Preferred peptide monomers usable in the present invention are illustrated below taking WT1 as an example. As used herein, the following one- or three-letter-abbreviations are used to shorten respective amino acid residues. Ala(A): alanine residue, Arg(R): arginine residue, Asn(N): asparagine residue, Asp(D): aspartic acid residue, Cys(C): cysteine residue, Gln(Q): glutamine residue, Glu(E): glutamic acid residue, Gly(G): glycine residue, His(H): histidine residue, Ile(I): isoleucine residue, Leu(L): leucine residue, Lys(K): lysine residue, Met(M): methionine residue, Phe(F): phenylalanine residue, Pro(P): proline residue, Ser(S): serine residue, Thr(T): threonine residue, Trp(W): tryptophan residue, Tyr(Y): tyrosine residue, Val(V): valine residue.

In the Table, the term "position" refers to the position of the peptide in human WT1.

TABLE 1

HLA-A 1-restricted Peptide Monomers

| Position | Amino acid sequence | SEQ ID NO: |
|---|---|---|
| 137-145 | CLESQPAIR | 2 |
| 80-88 | GAEPHEEQC | 3 |
| 354-362 | QCDFKDCER | 4 |
| 409-417 | TSEKPFSCR | 5 |
| 386-394 | KTCQRKFSR | 6 |
| 325-333 | CAYPGCNKR | 7 |
| 232-240 | QLECMTWNQ | 8 |
| 317-325 | TSEKRPFMC | 9 |

TABLE 2

HLA-A0201-restricted Peptide Monomers

| Position | Amino acid sequence | SEQ ID NO: |
|---|---|---|
| 280-288 | ILCGAQYRI | 10 |
| 235-243 | CMTWNQMNL | 11 |
| 227-235 | YQMTSQLEC | 12 |
| 408-416 | KTSEKPFSC | 13 |
| 228-236 | QMTSQLECM | 14 |
| 86-94 | EQCLSAFTV | 15 |

TABLE 3

HLA-A0205-restricted Peptide Monomers

| Position | Amino acid sequence | SEQ ID NO: |
|---|---|---|
| 235-243 | CMTWNQMNL | 11 |
| 227-235 | YQMTSQLEC | 12 |
| 194-202 | SVPPPVYGC | 16 |
| 280-288 | ILCGAQYRI | 10 |
| 81-89 | AEPHEEQCL | 17 |

TABLE 4

HLA-A24-restricted Peptide Monomers

| Position | Amino acid sequence | SEQ ID NO: |
|---|---|---|
| 356-364 | DFKDCERRF | 18 |
| 326-334 | AYPGCNKRY | 19 |
| 130-138 | NAPYLPSCL | 20 |
| 329-337 | GCNKRYFKL | 21 |
| 417-425 | RWPSCQKKF | 22 |
| 207-215 | DSCTGSQAL | 23 |
| 235-243 | CMTWNQMNL | 11 |
| 235*-243 | CYTWNQMNL | 44 |

*M at position 236 in SEQ ID NO: 11 is altered to Y.

TABLE 5

HLA-A3-restricted Peptide Monomers

| Position | Amino acid sequence | SEQ ID NO: |
|---|---|---|
| 88-96 | CLSAFTVHF | 24 |
| 137-145 | CLESQPAIR | 2 |
| 280-288 | ILCGAQYRI | 10 |
| 386-394 | KTCQRKFSR | 6 |
| 235-243 | CMTWNQMNL | 11 |
| 383-391 | FQCKTCQRK | 25 |
| 194-202 | SVPPPVYGC | 16 |

TABLE 6

HLA-A68.1-restricted Peptide Monomers

| Position | Amino acid sequence | SEQ ID NO: |
|---|---|---|
| 100-108 | FTGTAGACR | 26 |
| 386-394 | KTCQRKFSR | 6 |
| 409-417 | TSEKPFSCR | 5 |
| 325-333 | CAYPGCNKR | 7 |
| 354-362 | QCDFKDCER | 4 |
| 324-332 | MCAYPGCNK | 27 |
| 379-387 | GVKPFQCKT | 28 |
| 137-145 | CLESQPAIR | 2 |

TABLE 7

HLA-A1101-restricted Peptide Monomers

| Position | Amino acid sequence | SEQ ID NO: |
|---|---|---|
| 386-394 | KTCQRKFSR | 6 |
| 383-391 | FQCKTCQRK | 25 |

TABLE 7-continued

HLA-A1101-restricted Peptide Monomers

| Position | Amino acid sequence | SEQ ID NO: |
|---|---|---|
| 100-108 | FTGTAGACR | 26 |
| 324-332 | MCAYPGCNK | 27 |
| 415-423 | SCRWPSCQK | 29 |
| 137-145 | CLESQPAIR | 2 |
| 325-333 | CAYPGCNKR | 7 |

TABLE 8

HLA-A3101-restricted Peptide Monomers

| Position | Amino acid sequence | SEQ ID NO: |
|---|---|---|
| 386-394 | KTCQRKFSR | 6 |
| 137-145 | CLESQPAIR | 2 |
| 100-108 | FTGTAGACR | 26 |
| 325-333 | CAYPGCNKR | 7 |
| 279-287 | PILCGAQYR | 30 |
| 354-362 | QCDFKDCER | 4 |
| 383-391 | FQCKTCQRK | 25 |
| 358-366 | KDCERRFSR | 31 |

TABLE 9

HLA-A3302-restricted Peptide Monomers

| Position | Amino acid sequence | SEQ ID NO: |
|---|---|---|
| 409-417 | TSEKPFSCR | 5 |
| 137-145 | CLESQPAIR | 2 |
| 354-362 | QCDFKDCER | 4 |
| 100-108 | FTGTAGACR | 26 |
| 325-333 | CAYPGCNKR | 7 |
| 207-215 | DSCTGSQAL | 23 |
| 419-427 | PSCQKKFAR | 32 |

TABLE 10

HLA-B14-restricted Peptide Monomers

| Position | Amino acid sequence | SEQ ID NO: |
|---|---|---|
| 329-337 | GCNKRYFKL | 33 |

TABLE 11

HLA-B40-restricted Peptide Monomers

| Position | Amino acid sequence | SEQ ID NO: |
|---|---|---|
| 81-89 | AEPHEEQCL | 17 |
| 410-418 | SEKPFSCRW | 34 |

TABLE 11-continued

HLA-B40-restricted Peptide Monomers

| Position | Amino acid sequence | SEQ ID NO: |
|---|---|---|
| 318-326 | SEKRPFMCA | 35 |
| 233-241 | LECMTWNQM | 36 |
| 349-357 | GEKPYQCDF | 37 |
| 85-93 | EEQCLSAFT | 38 |
| 23-31 | GCALPVSGA | 39 |
| 206-214 | TDSCTGSQA | 40 |
| 24-32 | CALPVSGAA | 41 |
| 84-92 | HEEQCLSAF | 42 |

TABLE 12

HLA-B60-restricted Peptide Monomers

| Position | Amino acid sequence | SEQ ID NO: |
|---|---|---|
| 81-89 | AEPHEEQCL | 17 |
| 233-241 | LECMTWNQM | 36 |
| 209-217 | CTGSQALLL | 43 |
| 318-326 | SEKRPFMCA | 35 |
| 329-337 | GCNKRYFKL | 33 |
| 130-138 | NAPYLPSCL | 20 |
| 85-93 | EEQCLSAFT | 38 |
| 208-216 | SCTGSQALL | 45 |
| 207-215 | DSCTGSQAL | 23 |
| 18-26 | LGGGGGCAL | 46 |

TABLE 13

HLA-B61-restricted Peptide Monomers

| Position | Amino acid sequence | SEQ ID NO: |
|---|---|---|
| 318-326 | SEKRPFMCA | 35 |
| 81-89 | AEPHEEQCL | 17 |
| 233-241 | LECMTWNQM | 36 |
| 85-93 | EEQCLSAFT | 38 |
| 206-214 | TDSCTGSQA | 40 |
| 20-28 | GGGGCALPV | 47 |
| 23-31 | GCALPVSGA | 39 |

TABLE 14

HLA-B62-restricted Peptide Monomers

| Position | Amino acid sequence | SEQ ID NO: |
|---|---|---|
| 88-96 | CLSAFTVHF | 24 |
| 17-25 | SLGGGGGCA | 48 |
| 384-392 | QCKTCQRKF | 49 |
| 227-235 | YQMTSQLEC | 12 |
| 86-94 | EQCLSAFTV | 15 |
| 101-109 | TGTAGACRY | 50 |
| 280-288 | ILCGAQYRI | 10 |

TABLE 15

HLA-B7-restricted Peptide Monomers

| Position | Amino acid sequence | SEQ ID NO: |
|---|---|---|
| 130-138 | NAPYLPSCL | 20 |
| 208-216 | SCTGSQALL | 45 |
| 18-26 | LGGGGGCAL | 46 |
| 207-215 | DSCTGSQAL | 23 |
| 209-217 | CTGSQALLL | 43 |
| 329-337 | GCNKRYFKL | 33 |
| 235-243 | CMTWNQMNL | 11 |

TABLE 16

HLA-B8-restricted Peptide Monomers

| Position | Amino acid sequence | SEQ ID NO: |
|---|---|---|
| 329-337 | GCNKRYFKL | 33 |
| 208-216 | SCTGSQALL | 45 |
| 130-138 | NAPYLPSCL | 20 |
| 420-428 | SCQKKFARS | 51 |
| 387-395 | TCQRKFSRS | 52 |
| 207-215 | DSCTGSQAL | 23 |
| 384-392 | QCKTCQRKF | 49 |
| 136-144 | SCLESQPAI | 53 |
| 347-355 | HTGEKPYQC | 54 |

TABLE 17

HLA-B2702-restricted Peptide Monomers

| Position | Amino acid sequence | SEQ ID NO: |
|---|---|---|
| 416-424 | CRWPSCQKK | 55 |
| 107-115 | CRYGPFGPP | 56 |

TABLE 18

HLA-B2705-restricted Peptide Monomers

| Position | Amino acid sequence | SEQ ID NO: |
|---|---|---|
| 416-424 | CRWPSCQKK | 55 |
| 383-391 | FQCKTCQRK | 25 |

TABLE 19

HLA-B3501-restricted Peptide Monomers

| Position | Amino acid sequence | SEQ ID NO: |
|---|---|---|
| 278-286 | TPILCGAQY | 57 |
| 327-335 | YPGCNKRYF | 58 |
| 82-90 | EPHEEQCLS | 59 |
| 207-215 | DSCTGSQAL | 23 |
| 412-420 | KPFSCRWPS | 60 |

TABLE 20

HLA-B3701-restricted Peptide Monomers

| Position | Amino acid sequence | SEQ ID NO: |
|---|---|---|
| 81-89 | AEPHEEQCL | 17 |
| 85-93 | EEQCLSAFT | 38 |
| 208-216 | SCTGSQALL | 45 |
| 209-217 | CTGSQALLL | 43 |
| 206-214 | TDSCTGSQA | 40 |
| 84-92 | HEEQCLSAF | 42 |
| 233-241 | LECMTWNQM | 36 |
| 349-357 | GEKPYQCDF | 37 |

TABLE 21

HLA-B3801-restricted Peptide Monomers

| Position | Amino acid sequence | SEQ ID NO: |
|---|---|---|
| 202-210 | CHTPTDSCT | 61 |
| 417-425 | RWPSCQKKF | 22 |
| 327-335 | YPGCNKRYF | 58 |
| 208-216 | SCTGSQALL | 45 |
| 18-26 | LGGGGGCAL | 46 |
| 83-91 | PHEEQCLSA | 62 |

TABLE 22

HLA-B3901-restricted Peptide Monomers

| Position | Amino acid sequence | SEQ ID NO: |
|---|---|---|
| 136-144 | SCLESQPAI | 53 |
| 208-216 | SCTGSQALL | 45 |
| 207-215 | DSCTGSQAL | 23 |

TABLE 23

HLA-B3902-restricted Peptide Monomers

| Position | Amino acid sequence | SEQ ID NO: |
|---|---|---|
| 130-138 | NAPYLPSCL | 20 |
| 209-217 | CTGSQALLL | 43 |
| 207-215 | DSCTGSQAL | 23 |
| 208-216 | SCTGSQALL | 45 |
| 329-337 | GCNKRYFKL | 33 |

TABLE 24

HLA-B4403-restricted Peptide Monomers

| Position | Amino acid sequence | SEQ ID NO: |
|---|---|---|
| 349-357 | GEKPYQCDF | 37 |
| 84-92 | HEEQCLSAF | 42 |
| 410-418 | SEKPFSCRW | 34 |
| 278-286 | TPILCGAQY | 57 |
| 318-326 | SEKRPFMCA | 35 |
| 81-89 | AEPHEEQCL | 17 |
| 101-109 | TGTAGACRY | 50 |
| 85-93 | EEQCLSAFT | 38 |
| 233-241 | LECMTWNQM | 36 |
| 104-112 | AGACRYGPF | 63 |

TABLE 25

HLA-B5101-restricted Peptide Monomers

| Position | Amino acid sequence | SEQ ID NO: |
|---|---|---|
| 130-138 | NAPYLPSCL | 20 |
| 20-28 | GGGGCALPV | 47 |
| 18-26 | LGGGGGCAL | 46 |
| 418-426 | WPSCQKKFA | 64 |
| 82-90 | EPHEEQCLS | 59 |
| 280-288 | ILCGAQYRI | 10 |
| 204-212 | TPTDSCTGS | 65 |

TABLE 26

HLA-B5102-restricted Peptide Monomers

| Position | Amino acid sequence | SEQ ID NO: |
|---|---|---|
| 130-138 | NAPYLPSCL | 20 |
| 20-28 | GGGGCALPV | 47 |
| 412-420 | KPFSCRWPS | 60 |
| 18-26 | LGGGGGCAL | 46 |

TABLE 26-continued

HLA-B5102-restricted Peptide Monomers

| Position | Amino acid sequence | SEQ ID NO: |
|---|---|---|
| 24-32 | CALPVSGAA | 66 |
| 136-144 | SCLESQPAI | 53 |
| 418-426 | WPSCQKKFA | 64 |
| 351-359 | KPYQCDFKD | 67 |

TABLE 27

HLA-B5201-restricted Peptide Monomers

| Position | Amino acid sequence | SEQ ID NO: |
|---|---|---|
| 86-94 | EQCLSAFTV | 15 |
| 20-28 | GGGGCALPV | 47 |
| 327-335 | YPGCNKRYF | 58 |
| 104-112 | AGACRYGPF | 63 |

TABLE 28

HLA-B5801-restricted Peptide Monomers

| Position | Amino acid sequence | SEQ ID NO: |
|---|---|---|
| 230-238 | TSQLECMTW | 68 |
| 408-416 | KTSEKPFSC | 13 |
| 276-284 | HTTPILCGA | 69 |
| 347-355 | HTGEKPYQC | 54 |
| 317-325 | TSEKRPFMC | 9 |

TABLE 29

HLA-CW0301-restricted Peptide Monomers

| Position | Amino acid sequence | SEQ ID NO: |
|---|---|---|
| 329-337 | GCNKRYFKL | 21 |
| 24-32 | CALPVSGAA | 41 |
| 136-144 | SCLESQPAI | 53 |
| 130-138 | NAPYLPSCL | 20 |

TABLE 30

HLA-CW0401-restricted Peptide Monomers

| Position | Amino acid sequence | SEQ ID NO: |
|---|---|---|
| 356-364 | DFKDCERRF | 18 |
| 327-335 | YPGCNKRYF | 58 |
| 326-334 | AYPGCNKRY | 19 |
| 417-425 | RWPSCQKKF | 22 |

TABLE 30-continued

HLA-CW0401-restricted Peptide Monomers

| Position | Amino acid sequence | SEQ ID NO: |
|---|---|---|
| 278-286 | TPILCGAQY | 57 |
| 99-107 | QFTGTAGAC | 70 |

TABLE 31

HLA-CW0602-restricted Peptide Monomers

| Position | Amino acid sequence | SEQ ID NO: |
|---|---|---|
| 130-138 | NAPYLPSCL | 20 |
| 319-327 | EKRPFMCAY | 71 |
| 207-215 | DSCTGSQAL | 23 |

TABLE 32

HLA-CW0702-restricted Peptide Monomers

| Position | Amino acid sequence | SEQ ID NO: |
|---|---|---|
| 319-327 | EKRPFMCAY | 71 |
| 326-334 | AYPGCNKRY | 19 |
| 278-286 | TPILCGAQY | 57 |
| 327-335 | YPGCNKRYF | 58 |
| 101-109 | TGTAGACRY | 50 |
| 130-138 | NAPYLPSCL | 20 |
| 84-92 | HEEQCLSAF | 42 |

It has been known that there are many subtypes of HLA molecule and that the amino acid sequence of tumor antigen peptide that binds to each subtype obeys a certain rule (binding motif). The binding motif for HLA-A24 is known that, in the peptides consisting of 8 to 11 amino acid residues, the amino acid at position 2 is tyrosine (Tyr), phenylalanine (Phe), methionine (Met) or tryptophan (Trp), and the amino acid at the C-terminus is phenylalanine (Phe), leucine (Leu), isoleucine (Ile), tryptophan (Trp) or methionine (Met) (J. Immunol., 152, p3913, 1994, Immunogenetics, 41, p178, 1995, J. Immunol., 155, p4307, 1994). Accordingly, in addition to the peptide monomers in Table 4, a peptide monomer of the following formula can also be preferably used as an HLA-24-restricted peptide monomer.

(SEQ ID NO: 72)
Cys Xaa Thr Trp Asn Gln Met Asn Xaa wherein Xaa at position 2 is an amino acid residue selected from Tyr, Phe, Met and Trp; and Xaa at position 9 is an amino acid residue selected from Phe, Leu, Ile, Trp and Met.

The binding motif for HLA-A0201 is known that, in the peptides consisting of 8 to 11 amino acid residues, the amino acid at position 2 is leucine (Leu) or methionine (Met), and the amino acid at the C-terminus is valine (Val) or leucine (Leu). The binding motif for HLA-A0205 is known that, in the peptides consisting of 8 to 11 amino acid residues, the amino acid at position 2 is valine (Val), leucine (Leu), isoleucine(Ile) or methionine (Met) and the amino acid at the C terminus is leucine (Leu) (Immunogenetics, 41, p. 178, 1995; J. Immunol., 155: p. 4749, 1995). Accordingly, a peptide wherein the amino acid at position 2 or the C terminus of a peptide monomer shown in Table 2 or 3 above is substituted by any one of amino acid motifs described above can also be preferably used as an HLA-A0201- or HLA-A0205-restricted peptide monomer.

The peptide monomers shown in Table 4 above are especially preferred to be used in the present invention. Among the peptides in Table 4, the SEQ ID NO:44 is a non-natural variant peptide wherein the methionine at position 236 of SEQ ID NO: 11 (position 235-243) is altered to tyrosine. Accordingly, the peptide monomers of the present invention include those having a sequence wherein one or more amino acid residues other than cysteine residue are altered in the sequence of natural-type peptides and showing CTL inducing activity.

As another embodiment, the present invention provides a pharmaceutical composition comprising a peptide dimer of the present invention together with a therapeutically acceptable carrier therefor. Although the amount of a peptide dimer of the present invention as an active ingredient in the pharmaceutical composition may vary depending on the purpose of treatment, the age, weight of the patient, and the like, it is typically 0.0001 mg to 1000 mg, preferably 0.001 mg to 1000 mg, more preferably 0.1 mg to 20 mg.

The pharmaceutical composition of the present invention may comprise, as an active ingredient, a peptide monomer in addition to a peptide dimer of the present invention. There is no limitation about the content of a "peptide dimer" in the pharmaceutical composition of the present invention on the condition that the CTL inducing activity is exerted; however, it can be 50% or more, preferably 70-100%, and more preferably 80-100% of the whole peptides. The content of a peptide dimer can be confirmed by high performance liquid chromatography (HPLC).

The pharmaceutically acceptable carriers are those being capable of enhancing the cellular immunity. Such carriers include an adjuvant. Examples of adjuvant applicable to the present invention include those described in a literature (Clin. Microbiol. Rev., 7: 277-289, 1994), specifically, components derived from microorganisms, cytokines, components derived from plants, mineral gels such as aluminium hydroxide, lysolecithin, surfactants such as Pluronic® polyols, polyanion, peptide, oil emulsion (emulsion preparation) and the like. Also, the carrier includes components required for the preparation of liposomal preparations, particulate preparations in which the ingredient is bound to beads having a diameter of several μm, preparations in which the ingredient is attached to lipids, and the like.

Administration may be achieved, for example, intradermally, subcutaneously, intramuscularly, or intravenously. Preferred route is intradermal or subcutaneous administration that induces CTLs efficiently. The frequency or interval of administration can be adjusted appropriately depending on the disease to be treated or prevented, and individual difference; however, the administration is preferably carried out more than one times at an interval of once in a several days to several months.

For example, when the pharmaceutical composition of the present invention comprising a peptide dimer consisting of peptide monomers derived from WT1 is administered to a WT1-positive patient, the peptide is presented to an HLA antigen of antigen-presenting cells to form a complex. CTLs specific for the presented HLA antigen complex are then proliferated and destroy cancer cells, whereby cancer can be treated or prevented. The pharmaceutical composition of the present invention can be used to treat or prevent cancers associated by the elevated expression level of WT1 gene including blood cancers such as leukemia, myelodysplastic syndrome, multiple myeloma and malignant lymphoma, and solid cancers such as gastric cancer, colon cancer, lung cancer, breast cancer, embryonal cancer, hepatic cancer, skin cancer, bladder cancer, prostate cancer, uterine cancer, cervical cancer, and ovarian cancer.

In the further embodiment, the present invention provides a method for treating or preventing cancers by administering the pharmaceutical composition of the present invention to a WT1-positive patient.

EXAMPLES

The present invention is further illustrated by the following examples, but is not limited by these examples in any respect.

Preparation 1

1. Synthesis of Protected Peptide Resin (H-Cys(Trt)-Tyr(Trt)-Thr(tBu)-Trp(Boc)-Asn(Trt)-Gln(Trt)-Met-Asn(Trt)-Leu-Alko-Resin)

Fmoc-Leu-Alko-resin (wherein Alko is p-alkoxybenzyl alcohol) (12 g) (0.81 mmol/g, Watanabe Chemical Industries, Ltd.) was charged in a reaction vessel (500 ml, Type ACT90 solid phase synthesizer, Advanced ChemTech) and washed once with DMF or the like (Process 1). The resin was then treated with 25% Pip (piperidine) (3 minutes×1, and 15 minutes×1) to cleave the Fmoc group (Process 2), and washed again with DMF or the like (Process 1) to remove Pip. To the reaction vessel was added a solution of Fmoc-Asn(Trt)-OH (29.36 g) and HOBT (1-hydroxybenzotriazole) (7.5 g) in NMP (N-methylpyrrolidinone) (150 ml). After adding DIPCI (N,N'-diisopropylcarbodiimide) (7.6 ml), the mixture was stirred at room temperature for 30 minutes (Process 3). Thirty minutes later, the resin was washed with NMP (Process 4), and subjected to the coupling reaction once again using Fmoc-Asn(Trt)-OH (29.36 g) and HOBT (7.5 g) (Process 5) to synthesize Fmoc-Asn(Trt)-Leu-Alko resin. The resultant resin was then converted to H-Asn(Trt)-Leu-Alko-resin by repeating the deprotection of Process 2. After washing (Process 1), Fmoc-Met-OH (18.27 g), Fmoc-Gln(Trt)-OH (30.04 g), Fmoc-Asn(Trt)-OH (29.36 g), Fmoc-Trp(Boc)-OH (25.91 g), Fmoc-Thr(tBu)—OH (19.56 g), Fmoc-Tyr(tBu)—OH (22.60 g) and Fmoc-Cys(Trt)-OH (28.82 g) were added in series to conduct the coupling reaction (Process 3), wherein the coupling was repeated three times with Fmoc-Thr(tBu)—OH. The resultant resin was washed with DMF and treated with 25% AC$_2$O (acetic anhydride) (15 minutes×2) for the capping of unreacted amino groups. Following condensation of the N-terminal Fmoc-Cys(Trt)-OH, the deprotection (Process 2) and washing (Process 6) were conducted to obtain H-Cys(Trt)-Tyr(Trt)-Thr(tBu)-Trp(Boc)-Asn(Trt)-Gln(Trt)-Met-Asn(Trt)-Leu-Alko-Resin. The above processes for synthesis are summarized in Table 33.

TABLE 33

<Processes for Synthesis>

| Process | Reagent | Number of treatment | Time (min) |
|---|---|---|---|
| 1) Washing | DMF | 100 ml × 6 | 0.3 |
| | MeOH | 100 ml × 1 | 0.3 |
| | DMF | 100 ml × 3 | 0.3 |

TABLE 33-continued

<Processes for Synthesis>

| Process | Reagent | Number of treatment | Time (min) |
|---|---|---|---|
| 2) Deprotection | 25% piperidine/DMF | 100 ml | 3.0 |
| | | 100 ml | 15.0 |
| 3) Coupling | Amino-protected amino acid (5 eq. for each), HOBT (5 eq.), DIPCI (5 eq.)/NMP | 150 ml | 30 × 1 |
| 4) Washing | NMP | 100 ml × 2 | 0.3 |
| 5) Coupling | Amino-protected amino acid (5 eq. for each), HOBT (5 eq.), DIPCI (5 eq.)/NMP | 150 ml | 30 × 1 |
| 6) Washing | DMF | 100 ml × 5 | 0.3 |
| | MeOH | 100 ml × 1 | 0.3 |
| | DMF | 100 ml × 2 | 0.3 |

2. Deprotection of Protected Peptide Resin protected peptide resin (H-Cys(Trt)-Tyr(Trt)-Thr(tBu)-Trp(Boc)-Asn(Trt)-Gln(Trt)-Met-Asn(Trt)-Leu-Alko-Resin) (14.06 g) obtained in accordance with the processes above were added Reagent K (5% phenol/5% thioanisole/5% H$_2$O/2.5% ethanediol/TFA solution, 100 ml) and triisopropylsilane (TIPS, 15 ml), and the mixture was stirred at room temperature for 2.5 hours. After adding diethyl ether (ca. 500 ml), the mixture was filtered through a glass filter to remove Reagent K and diethyl ether as filtrate. The residue on the filter was washed with diethyl ether (ca. 100 ml, ×3) followed by addition of TFA (ca. 100 ml×3) to obtain filtrate (300 ml) containing the objective product. The filtrate was concentrated to remove TFA and lyophilized after adding acetonitrile (ca. 50 ml) and 20% aqueous acetic acid solution (ca. 250 ml) to obtain a crude peptide (H-Cys-Tyr-Thr-Trp-Asn-Gln-Met-Asn-Leu-OH, SEQ ID NO:44) (6.12 g) as powder.

3. Purification of Crude Peptide

The resultant crude peptide (749 mg) was dissolved in TFA (10 ml) and charged onto ODS C$_{18}$ column (5 cm Φ×50 cm L, YMC, Co., Ltd.) of HPLC (Shimadzu; LC8AD type) equilibrated with solution 1 (=H$_2$O/0.1% TFA) using an HPLC pump. The column was kept for about 30 minutes as it is, and then the concentration of solution 2 (=CH$_3$CN/0.1% TFA) was increased from 0% to 15% over 30 minutes. Thereafter, the concentration of solution 2 was increased upto 28% over 330 minutes, while the eluate containing the objective peptide was monitored by UV absorption at 220 nm to collect the fractions containing the objective product. The fractions were combined and injected into ODS C$_{18}$ column (4.6 mm Φ×25 cm L, YMC, Co., Ltd.) attached to HPLC (Hitachi, L-4000 type) and equilibrated with 17% solution 2 (=CH$_3$CN/0.1% TFA) in a mixture of solution 1 (=H$_2$O/0.1% TFA) and solution 2 (=CH$_3$CN/0.1% TFA), and then the concentration of solution 2 was increased upto 47% over 30 minutes while monitoring the eluate by UV absorption at 220 nm over 30 minutes to obtain the purified objective peptide monomer (227.5 mg) with retention time of 14.79 minutes.

Amino Acid Analysis

Hydrolysis: 1% phenol/6N aqueous hydrochloric acid solution 110° C., 10 hours

Analytical method: ninhydrin method

Asx:1.71(2) Thr:0.75(1) Glx:1.07(1) Met:0.91(1)*Leu:(1) Tyr:0.82(1)

*) Leu=reference amino acid

The value in parentheses ( ): theoretical value

Mass spectrometry: LC/MS M$^{+1}$=1173.0 (theoretical value=1172.36)

Peptide Sequencing: sequence was confirmed from the second residue (Tyr) from the N-terminus to the C-terminus, Leu, successively.

Example 1

Synthesis of a Dimer of the Formula

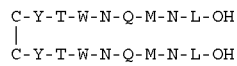

Air oxidization was conducted by stirring a mixture of a peptide monomer (227.5 mg) prepared in Preparation 1, N-methylglucamine (NMG) (227.5 mg) and water (23 ml) at room temperature for about 2 days. To the reaction solution was added an aqueous solution of sodium acetate (2 g) in water (5 ml), and the mixture was stirred at room temperature for about 20 minutes. After adding water (200 ml) and acetonitrile (ca. 200 ml), the mixture was filtered through Kiriyama Roht (filter paper No. 5C), and the residue on the filter was washed with water (ca. 50 ml×3). The residue on the filter was collected and lyophilized after adding water (ca. 200 ml) to obtain the crude product of objective peptide dimer (158 mg).
Purification of Crude Peptide Dimer Crude peptide dimer (158 mg) was dissolved in DMSO (9 ml) and charged onto ODS $C_{18}$ column (5 cm Φ×50 cm L, YMC, Co., Ltd.) of HPLC (Shimadzu; LC8AD type) equilibrated with solution 1 (=$H_2$O/1% AcOH) using a HPLC pump. The column was kept for about 30 minutes as it is, and then the concentration of solution 2 (=$CH_3$CN/1% AcOH) was increased from 0% to 40% over 360 minutes. Thereafter, the fractions containing the objective product were collected by means of automatic fraction collector while monitoring the eluate containing the objective peptide dimer by UV absorption at 220 nm. The fractions were combined and injected into ODS $C_{18}$ column (4.6 mm Φ×25 cm L, YMC, Co., Ltd.) attached to HPLC (Hitachi, L-4000 type) and equilibrated with 17% solution 2 (=$CH_3$CN/0.1% TFA) in a mixture of solution 1 (=$H_2$O/0.1% TFA) and solution 2 (=$CH_3$CN/0.1% TFA). The concentration of solution 2 was then increased from 0% to 47% while monitoring the eluate by UV absorption at 220 nm over 30 minutes to obtain the purified objective peptide dimer (46.6 mg) with retention time of 20.51 minutes.

FAB.MS 2365.0 (theoretical value: 2342.70) $Na^+$ F=0.25%

Test Example 1

Induction of CTLs with Peptide Dimer

The CTL-inducing activity of the peptide dimer prepared in Example 1 was evaluated using HLA-A24 transgenic mice (Int. J. Cancer: 100, 565, 2002). The peptide dimer was dissolved in dimethyl sulfoxide (DMSO) to obtain a 40 mg/ml peptide solution. The peptide solution (35 μl) was then added to 10 mM phosphate buffer (pH 7.5) (581 μl) to obtain a peptide suspension. The resultant peptide suspension (550 μl) and Montanide ISA51 (Seppic) (700 μl) were mixed using a connected glass syringe to prepare an emulsion as an administration solution.

The administration solution (200 μl) was injected into an HLA-A24 transgenic mouse subcutaneously in the base of the tail. Three mice were used. Seven days after the injection, the spleen was removed and splenocytes were prepared. A portion of the splenocytes was pulsed with the peptide dimer (100 μg/ml) for 1 hour. Splenocytes not pulsed with the peptide were seeded into a 24-well plate at $7×10^6$ cells/well and thereto were added the above-mentioned splenocytes pulsed with the peptide ($1×10^6$ cells/well), and the plate was incubated. The incubation was conducted in RPMI1640 medium supplemented with 10% FCS, 10 mM HEPES, 20 mM L-glutamine, 1 mM sodium pyruvate, 1 mM MEM nonessential amino acids, 1% MEM vitamin and 55 μM 2-mercaptoethanol for 5 days.

The cultured splenocytes were examined for the cytotoxic activity specific for the peptide used in the administration by $^{51}$Cr release assay (J. Immunol.: 159, 4753, 1997). EL4-A2402/$K^b$ cells obtained by transforming EL-4 cells (ATCC No. TIB-39) in such a manner that a chimera MHC class I molecule of HLA-A24 and H2$K^b$ (Int. J. Cancer: 100, 565, 20002) are expressed stably were used as the target cells. The target cells were labeled with $^{51}$Cr (3.7 MBq/$10^6$ cells) and pulsed with the peptide at 100 μg/ml for an hour. For control, target cells not pulsed with the peptide were labeled with $^{51}$Cr for 2 hours. Those labeled target cells and the previously prepared splenocytes were mixed at a ratio of 1:120, cultured for 4 hours and the CTL activity was evaluated on the basis of the percent of damaged target cells. The results are shown in FIG. 1. The splenocytes prepared from the mouse injected with the peptide injured strongly the target cells pulsed with the peptide. However, they showed only weak cytotoxicity on the target cells not pulsed with the peptide. These results clearly showed that CTLs specific for the peptide were induced.

Industrial Applicability

According to the present invention, a peptide dimer having a CTL-inducing activity in vivo, and pharmaceutical compositions comprising the same as an active ingredient are provided. The present invention can be useful in the improvement of conditions of many tumor patients.

The invention claimed is:

1. A method of inducing cytotoxic T-lymphocytes in a patient, which comprises administering an effective amount of a peptide homodimer to the patient, wherein two peptide monomers of the peptide homodimer are selected from the peptide Cys Met Thr Trp Asn Gln Met Asn Leu (SEQ ID NO: 11) and the peptide Cys Tyr Thr Trp Asn Gln Met Asn Leu (SEQ ID NO: 44) and wherein the two peptide monomers are bound to each other through at least one disulfide bond to form the homodimer.

2. The method according to claim 1, wherein the peptide homodimer is

```
                                          (SEQ ID No: 44)
Cys Tyr Thr Trp Asn Gln Met Asn Leu
 |                                        (SEQ ID No: 44)
Cys Tyr Thr Trp Asn Gln Met Asn Leu.
```

3. A method of increasing stability of a peptide monomer in blood plasma, which comprises forming a homodimer of two peptide monomers, wherein the peptide monomers are selected from the peptide Cys Met Thr Trp Asn Gln Met Asn Leu (SEQ ID NO: 11) and the peptide Cys Tyr Thr Trp Asn Gln Met Asn Leu (SEQ ID NO: 44) and wherein the two peptide monomers are bound to each other through at least one disulfide bond to form the homodimer.

4. The method according to claim 3, wherein the peptide homodimer is

```
                                          (SEQ ID No: 44)
Cys Tyr Thr Trp Asn Gln Met Asn Leu
 |                                        (SEQ ID No: 44)
Cys Tyr Thr Trp Asn Gln Met Asn Leu.
```

\* \* \* \* \*

SEQUENCE LISTING

<160> NUMBER OF SEQ ID NOS: 72

<210> SEQ ID NO 1
<211> LENGTH: 449
<212> TYPE: PRT
<213> ORGANISM: Artificial
<220> FEATURE:
<223> OTHER INFORMATION: Synthetic Peptide

<400> SEQUENCE: 1

Met Gly Ser Asp Val Arg Asp Leu Asn Ala Leu Leu Pro Ala Val Pro
 1               5                  10                  15

-continued

```
Ser Leu Gly Gly Gly Gly Cys Ala Leu Pro Val Ser Gly Ala Ala
         20                  25                  30

Gln Trp Ala Pro Val Leu Asp Phe Ala Pro Pro Gly Ala Ser Ala Tyr
     35                  40                  45

Gly Ser Leu Gly Gly Pro Ala Pro Pro Ala Pro Pro Pro Pro
 50                  55                  60

Pro Pro Pro Pro His Ser Phe Ile Lys Gln Glu Pro Ser Trp Gly Gly
 65                  70                  75                  80

Ala Glu Pro His Glu Glu Gln Cys Leu Ser Ala Phe Thr Val His Phe
             85                  90                  95

Ser Gly Gln Phe Thr Gly Thr Ala Gly Ala Cys Arg Tyr Gly Pro Phe
                100                 105                 110

Gly Pro Pro Pro Ser Gln Ala Ser Ser Gly Gln Ala Arg Met Phe
        115                 120                 125

Pro Asn Ala Pro Tyr Leu Pro Ser Cys Leu Glu Ser Gln Pro Ala Ile
    130                 135                 140

Arg Asn Gln Gly Tyr Ser Thr Val Thr Phe Asp Gly Thr Pro Ser Tyr
145                 150                 155                 160

Gly His Thr Pro Ser His His Ala Ala Gln Phe Pro Asn His Ser Phe
                165                 170                 175

Lys His Glu Asp Pro Met Gly Gln Gln Gly Ser Leu Gly Glu Gln Gln
            180                 185                 190

Tyr Ser Val Pro Pro Val Tyr Gly Cys His Thr Pro Thr Asp Ser
        195                 200                 205

Cys Thr Gly Ser Gln Ala Leu Leu Leu Arg Thr Pro Tyr Ser Ser Asp
210                 215                 220

Asn Leu Tyr Gln Met Thr Ser Gln Leu Glu Cys Met Thr Trp Asn Gln
225                 230                 235                 240

Met Asn Leu Gly Ala Thr Leu Lys Gly Val Ala Ala Gly Ser Ser Ser
                245                 250                 255

Ser Val Lys Trp Thr Glu Gly Gln Ser Asn His Ser Thr Gly Tyr Glu
            260                 265                 270

Ser Asp Asn His Thr Thr Pro Ile Leu Cys Gly Ala Gln Tyr Arg Ile
        275                 280                 285

His Thr His Gly Val Phe Arg Gly Ile Gln Asp Val Arg Arg Val Pro
    290                 295                 300

Gly Val Ala Pro Thr Leu Val Arg Ser Ala Ser Glu Thr Ser Glu Lys
305                 310                 315                 320

Arg Pro Phe Met Cys Ala Tyr Pro Gly Cys Asn Lys Arg Tyr Phe Lys
                325                 330                 335

Leu Ser His Leu Gln Met His Ser Arg Lys His Thr Gly Glu Lys Pro
            340                 345                 350

Tyr Gln Cys Asp Phe Lys Asp Cys Glu Arg Arg Phe Ser Arg Ser Asp
        355                 360                 365

Gln Leu Lys Arg His Gln Arg Arg His Thr Gly Val Lys Pro Phe Gln
    370                 375                 380

Cys Lys Thr Cys Gln Arg Lys Phe Ser Arg Ser Asp His Leu Lys Thr
385                 390                 395                 400

His Thr Arg Thr His Thr Gly Lys Thr Ser Glu Lys Pro Phe Ser Cys
                405                 410                 415

Arg Trp Pro Ser Cys Gln Lys Lys Phe Ala Arg Ser Asp Glu Leu Val
            420                 425                 430

Arg His His Asn Met His Gln Arg Asn Met Thr Lys Leu Gln Leu Ala
        435                 440                 445
```

Leu

<210> SEQ ID NO 2
<211> LENGTH: 9
<212> TYPE: PRT
<213> ORGANISM: Artificial
<220> FEATURE:
<223> OTHER INFORMATION: Synthetic Peptide

<400> SEQUENCE: 2

Cys Leu Glu Ser Gln Pro Ala Ile Arg
1               5

<210> SEQ ID NO 3
<211> LENGTH: 9
<212> TYPE: PRT
<213> ORGANISM: Artificial
<220> FEATURE:
<223> OTHER INFORMATION: Synthetic Peptide

<400> SEQUENCE: 3

Gly Ala Glu Pro His Glu Glu Gln Cys
1               5

<210> SEQ ID NO 4
<211> LENGTH: 9
<212> TYPE: PRT
<213> ORGANISM: Artificial
<220> FEATURE:
<223> OTHER INFORMATION: Synthetic Peptide

<400> SEQUENCE: 4

Gln Cys Asp Phe Lys Asp Cys Glu Arg
1               5

<210> SEQ ID NO 5
<211> LENGTH: 9
<212> TYPE: PRT
<213> ORGANISM: Artificial
<220> FEATURE:
<223> OTHER INFORMATION: Synthetic Peptide

<400> SEQUENCE: 5

Thr Ser Glu Lys Pro Phe Ser Cys Arg
1               5

<210> SEQ ID NO 6
<211> LENGTH: 9
<212> TYPE: PRT
<213> ORGANISM: Artificial
<220> FEATURE:
<223> OTHER INFORMATION: Synthetic Peptide

<400> SEQUENCE: 6

Lys Thr Cys Gln Arg Lys Phe Ser Arg
1               5

<210> SEQ ID NO 7
<211> LENGTH: 9
<212> TYPE: PRT
<213> ORGANISM: Artificial
<220> FEATURE:
<223> OTHER INFORMATION: Synthetic Peptide

<400> SEQUENCE: 7

Cys Ala Thr Pro Gly Cys Asn Lys Arg
1               5

```
<210> SEQ ID NO 8
<211> LENGTH: 9
<212> TYPE: PRT
<213> ORGANISM: Artificial
<220> FEATURE:
<223> OTHER INFORMATION: Synthetic Peptide

<400> SEQUENCE: 8

Gln Leu Glu Cys Met Thr Trp Asn Gln
1               5

<210> SEQ ID NO 9
<211> LENGTH: 9
<212> TYPE: PRT
<213> ORGANISM: Artificial
<220> FEATURE:
<223> OTHER INFORMATION: Synthetic Peptide

<400> SEQUENCE: 9

Thr Ser Glu Lys Arg Pro Phe Met Cys
1               5

<210> SEQ ID NO 10
<211> LENGTH: 9
<212> TYPE: PRT
<213> ORGANISM: Artificial
<220> FEATURE:
<223> OTHER INFORMATION: Synthetic Peptide

<400> SEQUENCE: 10

Ile Leu Cys Gly Ala Gln Tyr Arg Ile
1               5

<210> SEQ ID NO 11
<211> LENGTH: 9
<212> TYPE: PRT
<213> ORGANISM: Artificial
<220> FEATURE:
<223> OTHER INFORMATION: Synthetic Peptide

<400> SEQUENCE: 11

Cys Met Thr Trp Asn Gln Met Asn Leu
1               5

<210> SEQ ID NO 12
<211> LENGTH: 9
<212> TYPE: PRT
<213> ORGANISM: Artificial
<220> FEATURE:
<223> OTHER INFORMATION: Synthetic Peptide

<400> SEQUENCE: 12

Tyr Gln Met Thr Ser Gln Leu Glu Cys
1               5

<210> SEQ ID NO 13
<211> LENGTH: 9
<212> TYPE: PRT
<213> ORGANISM: Artificial
<220> FEATURE:
<223> OTHER INFORMATION: Synthetic Peptide

<400> SEQUENCE: 13

Lys Thr Ser Glu Lys Pro Phe Ser Cys
1               5
```

```
<210> SEQ ID NO 14
<211> LENGTH: 9
<212> TYPE: PRT
<213> ORGANISM: Artificial
<220> FEATURE:
<223> OTHER INFORMATION: Synthetic Peptide

<400> SEQUENCE: 14

Gln Met Thr Ser Gln Leu Glu Cys Met
1               5

<210> SEQ ID NO 15
<211> LENGTH: 9
<212> TYPE: PRT
<213> ORGANISM: Artificial
<220> FEATURE:
<223> OTHER INFORMATION: Synthetic Peptide

<400> SEQUENCE: 15

Glu Gln Cys Leu Ser Ala Phe Thr Val
1               5

<210> SEQ ID NO 16
<211> LENGTH: 9
<212> TYPE: PRT
<213> ORGANISM: Artificial
<220> FEATURE:
<223> OTHER INFORMATION: Synthetic Peptide

<400> SEQUENCE: 16

Ser Val Pro Pro Pro Val Tyr Gly Cys
1               5

<210> SEQ ID NO 17
<211> LENGTH: 9
<212> TYPE: PRT
<213> ORGANISM: Artificial
<220> FEATURE:
<223> OTHER INFORMATION: Synthetic Peptide

<400> SEQUENCE: 17

Ala Glu Pro His Glu Glu Gln Cys Leu
1               5

<210> SEQ ID NO 18
<211> LENGTH: 9
<212> TYPE: PRT
<213> ORGANISM: Artificial
<220> FEATURE:
<223> OTHER INFORMATION: Synthetic Peptide

<400> SEQUENCE: 18

Asp Phe Lys Asp Cys Glu Arg Arg Phe
1               5

<210> SEQ ID NO 19
<211> LENGTH: 9
<212> TYPE: PRT
<213> ORGANISM: Artificial
<220> FEATURE:
<223> OTHER INFORMATION: Synthetic Peptide

<400> SEQUENCE: 19

Ala Tyr Pro Gly Cys Asn Lys Arg Tyr
1               5

<210> SEQ ID NO 20
<211> LENGTH: 9
```

```
<212> TYPE: PRT
<213> ORGANISM: Artificial
<220> FEATURE:
<223> OTHER INFORMATION: Synthetic Peptide

<400> SEQUENCE: 20

Asn Ala Pro Tyr Leu Pro Ser Cys Leu
1               5

<210> SEQ ID NO 21
<211> LENGTH: 9
<212> TYPE: PRT
<213> ORGANISM: Artificial
<220> FEATURE:
<223> OTHER INFORMATION: Synthetic Peptide

<400> SEQUENCE: 21

Gly Cys Asn Lys Arg Tyr Phe Lys Leu
1               5

<210> SEQ ID NO 22
<211> LENGTH: 9
<212> TYPE: PRT
<213> ORGANISM: Artificial
<220> FEATURE:
<223> OTHER INFORMATION: Synthetic Peptide

<400> SEQUENCE: 22

Arg Trp Pro Ser Cys Gln Lys Lys Phe
1               5

<210> SEQ ID NO 23
<211> LENGTH: 9
<212> TYPE: PRT
<213> ORGANISM: Artificial
<220> FEATURE:
<223> OTHER INFORMATION: Synthetic Peptide

<400> SEQUENCE: 23

Asp Ser Cys Thr Gly Ser Gln Ala Leu
1               5

<210> SEQ ID NO 24
<211> LENGTH: 9
<212> TYPE: PRT
<213> ORGANISM: Artificial
<220> FEATURE:
<223> OTHER INFORMATION: Synthetic Peptide

<400> SEQUENCE: 24

Cys Leu Ser Ala Phe Thr Val His Phe
1               5

<210> SEQ ID NO 25
<211> LENGTH: 9
<212> TYPE: PRT
<213> ORGANISM: Artificial
<220> FEATURE:
<223> OTHER INFORMATION: Synthetic Peptide

<400> SEQUENCE: 25

Phe Gln Cys Lys Thr Cys Gln Arg Lys
1               5

<210> SEQ ID NO 26
<211> LENGTH: 9
<212> TYPE: PRT
<213> ORGANISM: Artificial
```

```
<220> FEATURE:
<223> OTHER INFORMATION: Synthetic Peptide

<400> SEQUENCE: 26

Phe Thr Gly Thr Ala Gly Ala Cys Arg
1               5

<210> SEQ ID NO 27
<211> LENGTH: 9
<212> TYPE: PRT
<213> ORGANISM: Artificial
<220> FEATURE:
<223> OTHER INFORMATION: Synthetic Peptide

<400> SEQUENCE: 27

Met Cys Ala Tyr Pro Gly Cys Asn Lys
1               5

<210> SEQ ID NO 28
<211> LENGTH: 9
<212> TYPE: PRT
<213> ORGANISM: Artificial
<220> FEATURE:
<223> OTHER INFORMATION: Synthetic Peptide

<400> SEQUENCE: 28

Gly Val Lys Pro Phe Gln Cys Lys Thr
1               5

<210> SEQ ID NO 29
<211> LENGTH: 9
<212> TYPE: PRT
<213> ORGANISM: Artificial
<220> FEATURE:
<223> OTHER INFORMATION: Synthetic Peptide

<400> SEQUENCE: 29

Ser Cys Arg Trp Pro Ser Cys Gln Lys
1               5

<210> SEQ ID NO 30
<211> LENGTH: 9
<212> TYPE: PRT
<213> ORGANISM: Artificial
<220> FEATURE:
<223> OTHER INFORMATION: Synthetic Peptide

<400> SEQUENCE: 30

Pro Ile Leu Cys Gly Ala Gln Tyr Arg
1               5

<210> SEQ ID NO 31
<211> LENGTH: 9
<212> TYPE: PRT
<213> ORGANISM: Artificial
<220> FEATURE:
<223> OTHER INFORMATION: Synthetic Peptide

<400> SEQUENCE: 31

Lys Asp Cys Glu Arg Arg Phe Ser Arg
1               5

<210> SEQ ID NO 32
<211> LENGTH: 9
<212> TYPE: PRT
<213> ORGANISM: Artificial
<220> FEATURE:
<223> OTHER INFORMATION: Synthetic Peptide
```

```
<400> SEQUENCE: 32

Pro Ser Cys Gln Lys Lys Phe Ala Arg
1               5

<210> SEQ ID NO 33
<211> LENGTH: 9
<212> TYPE: PRT
<213> ORGANISM: Artificial
<220> FEATURE:
<223> OTHER INFORMATION: Synthetic Peptide

<400> SEQUENCE: 33

Gly Cys Asn Lys Arg Tyr Phe Lys Leu
1               5

<210> SEQ ID NO 34
<211> LENGTH: 9
<212> TYPE: PRT
<213> ORGANISM: Artificial
<220> FEATURE:
<223> OTHER INFORMATION: Synthetic Peptide

<400> SEQUENCE: 34

Ser Glu Lys Pro Phe Ser Cys Arg Trp
1               5

<210> SEQ ID NO 35
<211> LENGTH: 9
<212> TYPE: PRT
<213> ORGANISM: Artificial
<220> FEATURE:
<223> OTHER INFORMATION: Synthetic Peptide

<400> SEQUENCE: 35

Ser Glu Lys Arg Pro Phe Met Cys Ala
1               5

<210> SEQ ID NO 36
<211> LENGTH: 9
<212> TYPE: PRT
<213> ORGANISM: Artificial
<220> FEATURE:
<223> OTHER INFORMATION: Synthetic Peptide

<400> SEQUENCE: 36

Leu Glu Cys Met Thr Trp Asn Gln Met
1               5

<210> SEQ ID NO 37
<211> LENGTH: 9
<212> TYPE: PRT
<213> ORGANISM: Artificial
<220> FEATURE:
<223> OTHER INFORMATION: Synthetic Peptide

<400> SEQUENCE: 37

Gly Glu Lys Pro Tyr Gln Cys Asp Phe
1               5

<210> SEQ ID NO 38
<211> LENGTH: 9
<212> TYPE: PRT
<213> ORGANISM: Artificial
<220> FEATURE:
<223> OTHER INFORMATION: Synthetic Peptide

<400> SEQUENCE: 38
```

```
Glu Glu Gln Cys Leu Ser Ala Phe Thr
1               5
```

<210> SEQ ID NO 39
<211> LENGTH: 9
<212> TYPE: PRT
<213> ORGANISM: Artificial
<220> FEATURE:
<223> OTHER INFORMATION: Synthetic Peptide

<400> SEQUENCE: 39

```
Gly Cys Ala Leu Pro Val Ser Gly Ala
1               5
```

<210> SEQ ID NO 40
<211> LENGTH: 9
<212> TYPE: PRT
<213> ORGANISM: Artificial
<220> FEATURE:
<223> OTHER INFORMATION: Synthetic Peptide

<400> SEQUENCE: 40

```
Thr Asp Ser Cys Thr Gly Ser Gln Ala
1               5
```

<210> SEQ ID NO 41
<211> LENGTH: 9
<212> TYPE: PRT
<213> ORGANISM: Artificial
<220> FEATURE:
<223> OTHER INFORMATION: Synthetic Peptide

<400> SEQUENCE: 41

```
Cys Ala Leu Pro Val Ser Gly Ala Ala
1               5
```

<210> SEQ ID NO 42
<211> LENGTH: 9
<212> TYPE: PRT
<213> ORGANISM: Artificial
<220> FEATURE:
<223> OTHER INFORMATION: Synthetic Peptide

<400> SEQUENCE: 42

```
His Glu Glu Gln Cys Leu Ser Ala Phe
1               5
```

<210> SEQ ID NO 43
<211> LENGTH: 9
<212> TYPE: PRT
<213> ORGANISM: Artificial
<220> FEATURE:
<223> OTHER INFORMATION: Synthetic Peptide

<400> SEQUENCE: 43

```
Cys Thr Gly Ser Gln Ala Leu Leu Leu
1               5
```

<210> SEQ ID NO 44
<211> LENGTH: 9
<212> TYPE: PRT
<213> ORGANISM: Artificial
<220> FEATURE:
<223> OTHER INFORMATION: Synthetic Peptide

<400> SEQUENCE: 44

```
Cys Tyr Thr Trp Asn Gln Met Asn Leu
```

<210> SEQ ID NO 45
<211> LENGTH: 9
<212> TYPE: PRT
<213> ORGANISM: Artificial
<220> FEATURE:
<223> OTHER INFORMATION: Synthetic Peptide

<400> SEQUENCE: 45

Ser Cys Thr Gly Ser Gln Ala Leu Leu
1               5

<210> SEQ ID NO 46
<211> LENGTH: 9
<212> TYPE: PRT
<213> ORGANISM: Artificial
<220> FEATURE:
<223> OTHER INFORMATION: Synthetic Peptide

<400> SEQUENCE: 46

Leu Gly Gly Gly Gly Gly Cys Ala Leu
1               5

<210> SEQ ID NO 47
<211> LENGTH: 9
<212> TYPE: PRT
<213> ORGANISM: Artificial
<220> FEATURE:
<223> OTHER INFORMATION: Synthetic Peptide

<400> SEQUENCE: 47

Gly Gly Gly Gly Cys Ala Leu Pro Val
1               5

<210> SEQ ID NO 48
<211> LENGTH: 9
<212> TYPE: PRT
<213> ORGANISM: Artificial
<220> FEATURE:
<223> OTHER INFORMATION: Synthetic Peptide

<400> SEQUENCE: 48

Ser Leu Gly Gly Gly Gly Gly Cys Ala
1               5

<210> SEQ ID NO 49
<211> LENGTH: 9
<212> TYPE: PRT
<213> ORGANISM: Artificial
<220> FEATURE:
<223> OTHER INFORMATION: Synthetic Peptide

<400> SEQUENCE: 49

Gln Cys Lys Thr Cys Gln Arg Lys Phe
1               5

<210> SEQ ID NO 50
<211> LENGTH: 9
<212> TYPE: PRT
<213> ORGANISM: Artificial
<220> FEATURE:
<223> OTHER INFORMATION: Synthetic Peptide

<400> SEQUENCE: 50

Thr Gly Thr Ala Gly Ala Cys Arg Tyr
1               5

```
<210> SEQ ID NO 51
<211> LENGTH: 9
<212> TYPE: PRT
<213> ORGANISM: Artificial
<220> FEATURE:
<223> OTHER INFORMATION: Synthetic Peptide

<400> SEQUENCE: 51

Ser Cys Gln Lys Lys Phe Ala Arg Ser
1               5

<210> SEQ ID NO 52
<211> LENGTH: 9
<212> TYPE: PRT
<213> ORGANISM: Artificial
<220> FEATURE:
<223> OTHER INFORMATION: Synthetic Peptide

<400> SEQUENCE: 52

Thr Cys Gln Arg Lys Phe Ser Arg Ser
1               5

<210> SEQ ID NO 53
<211> LENGTH: 9
<212> TYPE: PRT
<213> ORGANISM: Artificial
<220> FEATURE:
<223> OTHER INFORMATION: Synthetic Peptide

<400> SEQUENCE: 53

Ser Cys Leu Glu Ser Gln Pro Ala Ile
1               5

<210> SEQ ID NO 54
<211> LENGTH: 9
<212> TYPE: PRT
<213> ORGANISM: Artificial
<220> FEATURE:
<223> OTHER INFORMATION: Synthetic Peptide

<400> SEQUENCE: 54

His Thr Gly Glu Lys Pro Tyr Gln Cys
1               5

<210> SEQ ID NO 55
<211> LENGTH: 9
<212> TYPE: PRT
<213> ORGANISM: Artificial
<220> FEATURE:
<223> OTHER INFORMATION: Synthetic Peptide

<400> SEQUENCE: 55

Cys Arg Trp Pro Ser Cys Gln Lys Lys
1               5

<210> SEQ ID NO 56
<211> LENGTH: 9
<212> TYPE: PRT
<213> ORGANISM: Artificial
<220> FEATURE:
<223> OTHER INFORMATION: Synthetic Peptide

<400> SEQUENCE: 56

Cys Arg Tyr Gly Pro Phe Gly Pro Pro
1               5

<210> SEQ ID NO 57
```

```
<211> LENGTH: 9
<212> TYPE: PRT
<213> ORGANISM: Artificial
<220> FEATURE:
<223> OTHER INFORMATION: Synthetic Peptide

<400> SEQUENCE: 57

Thr Pro Ile Leu Cys Gly Ala Gln Tyr
1               5

<210> SEQ ID NO 58
<211> LENGTH: 9
<212> TYPE: PRT
<213> ORGANISM: Artificial
<220> FEATURE:
<223> OTHER INFORMATION: Synthetic Peptide

<400> SEQUENCE: 58

Tyr Pro Gly Cys Asn Lys Arg Tyr Phe
1               5

<210> SEQ ID NO 59
<211> LENGTH: 9
<212> TYPE: PRT
<213> ORGANISM: Artificial
<220> FEATURE:
<223> OTHER INFORMATION: Synthetic Peptide

<400> SEQUENCE: 59

Glu Pro His Glu Glu Gln Cys Leu Ser
1               5

<210> SEQ ID NO 60
<211> LENGTH: 9
<212> TYPE: PRT
<213> ORGANISM: Artificial
<220> FEATURE:
<223> OTHER INFORMATION: Synthetic Peptide

<400> SEQUENCE: 60

Lys Pro Phe Ser Cys Arg Trp Pro Ser
1               5

<210> SEQ ID NO 61
<211> LENGTH: 9
<212> TYPE: PRT
<213> ORGANISM: Artificial
<220> FEATURE:
<223> OTHER INFORMATION: Synthetic Peptide

<400> SEQUENCE: 61

Cys His Thr Pro Thr Asp Ser Cys Thr
1               5

<210> SEQ ID NO 62
<211> LENGTH: 9
<212> TYPE: PRT
<213> ORGANISM: Artificial
<220> FEATURE:
<223> OTHER INFORMATION: Synthetic Peptide

<400> SEQUENCE: 62

Pro His Glu Glu Gln Cys Leu Ser Ala
1               5

<210> SEQ ID NO 63
<211> LENGTH: 9
<212> TYPE: PRT
```

```
<213> ORGANISM: Artificial
<220> FEATURE:
<223> OTHER INFORMATION: Synthetic Peptide

<400> SEQUENCE: 63

Ala Gly Ala Cys Arg Tyr Gly Pro Phe
1               5

<210> SEQ ID NO 64
<211> LENGTH: 9
<212> TYPE: PRT
<213> ORGANISM: Artificial
<220> FEATURE:
<223> OTHER INFORMATION: Synthetic Peptide

<400> SEQUENCE: 64

Trp Pro Ser Cys Gln Lys Lys Phe Ala
1               5

<210> SEQ ID NO 65
<211> LENGTH: 9
<212> TYPE: PRT
<213> ORGANISM: Artificial
<220> FEATURE:
<223> OTHER INFORMATION: Synthetic Peptide

<400> SEQUENCE: 65

Thr Pro Thr Asp Ser Cys Thr Gly Ser
1               5

<210> SEQ ID NO 66
<211> LENGTH: 9
<212> TYPE: PRT
<213> ORGANISM: Artificial
<220> FEATURE:
<223> OTHER INFORMATION: Synthetic Peptide

<400> SEQUENCE: 66

Cys Ala Leu Pro Val Ser Gly Ala Ala
1               5

<210> SEQ ID NO 67
<211> LENGTH: 9
<212> TYPE: PRT
<213> ORGANISM: Artificial
<220> FEATURE:
<223> OTHER INFORMATION: Synthetic Peptide

<400> SEQUENCE: 67

Lys Pro Tyr Gln Cys Asp Phe Lys Asp
1               5

<210> SEQ ID NO 68
<211> LENGTH: 9
<212> TYPE: PRT
<213> ORGANISM: Artificial
<220> FEATURE:
<223> OTHER INFORMATION: Synthetic Peptide

<400> SEQUENCE: 68

Thr Ser Gln Leu Glu Cys Met Thr Trp
1               5

<210> SEQ ID NO 69
<211> LENGTH: 9
<212> TYPE: PRT
<213> ORGANISM: Artificial
<220> FEATURE:
```

```
<223> OTHER INFORMATION: Synthetic Peptide

<400> SEQUENCE: 69

His Thr Thr Pro Ile Leu Cys Gly Ala
1               5

<210> SEQ ID NO 70
<211> LENGTH: 9
<212> TYPE: PRT
<213> ORGANISM: Artificial
<220> FEATURE:
<223> OTHER INFORMATION: Synthetic Peptide

<400> SEQUENCE: 70

Gln Phe Thr Gly Thr Ala Gly Ala Cys
1               5

<210> SEQ ID NO 71
<211> LENGTH: 9
<212> TYPE: PRT
<213> ORGANISM: Artificial
<220> FEATURE:
<223> OTHER INFORMATION: Synthetic Peptide

<400> SEQUENCE: 71

Glu Lys Arg Pro Phe Met Cys Ala Tyr
1               5

<210> SEQ ID NO 72
<211> LENGTH: 9
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Xaa = Tyr, Phe, Met or Trp
<220> FEATURE:
<221> NAME/KEY: MISC_FEATURE
<222> LOCATION: (9)..(9)
<223> OTHER INFORMATION: Xaa = Phe, Leu, Ile, Trp or Met

<400> SEQUENCE: 72

Cys Xaa Thr Trp Asn Gln Met Asn Xaa
1               5
```